(12) United States Patent
Fritz et al.

(10) Patent No.: US 10,219,946 B2
(45) Date of Patent: Mar. 5, 2019

(54) SPECKLE INTERFEROMETRIC METHOD AND SYSTEM FOR DETECTING A MOVEMENT OF A SURFACE

(75) Inventors: Andreas Fritz, Campow (DE); Ralf Brinkmann, Luebeck (DE)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 1265 days.

(21) Appl. No.: 14/373,255

(22) PCT Filed: Jan. 20, 2012

(86) PCT No.: PCT/EP2012/000263
§ 371 (c)(1),
(2), (4) Date: Jul. 18, 2014

(87) PCT Pub. No.: WO2013/107473
PCT Pub. Date: Jul. 25, 2013

(65) Prior Publication Data
US 2015/0011983 A1    Jan. 8, 2015

(51) Int. Cl.
| | | |
|---|---|---|
| *A61B 5/06* | (2006.01) | |
| *A61F 9/008* | (2006.01) | |
| *A61B 3/113* | (2006.01) | |
| *A61B 5/00* | (2006.01) | |
| *A61B 3/00* | (2006.01) | |
| *A61B 3/10* | (2006.01) | |

(52) U.S. Cl.
CPC ........ *A61F 9/00821* (2013.01); *A61B 3/0008* (2013.01); *A61B 3/10* (2013.01); *A61B 3/113* (2013.01); *A61B 5/0062* (2013.01); *A61B 5/0068* (2013.01); *A61F 2009/00844* (2013.01); *A61F 2009/00863* (2013.01)

(58) Field of Classification Search
CPC    A61B 3/008; A61B 3/10; A61B 3/113; A61B 5/0062; A61B 5/0068; A61F 9/00821; A61F 2009/00844; A61F 2009/0863
USPC .......................................................... 606/4
See application file for complete search history.

(56) References Cited

U.S. PATENT DOCUMENTS

| 6,830,567 B2 | 12/2004 | Schuele et al. |
|---|---|---|
| 7,836,894 B2 | 11/2010 | Brinkmann et al. |

(Continued)

FOREIGN PATENT DOCUMENTS

| EP | 1 643 924 B1 | 6/2011 |
|---|---|---|
| WO | WO 79/00841 A1 | 10/1979 |

(Continued)

OTHER PUBLICATIONS

International Search Report (PCT/ISA/210) dated Sep. 7, 2012 (Three (3) pages).

(Continued)

*Primary Examiner* — Aaron Roane
(74) *Attorney, Agent, or Firm* — Crowell & Moring LLP

(57) ABSTRACT

A method and a system for detecting a movement of a surface on an irradiated sample involves a light source for irradiating the surface with a coherent light beam, a detector for detecting variations caused by the movement in a speckle pattern produced by reflections of the light beam at the surface, selecting a single speckle from the speckle pattern, and detecting the variations at the selected speckle.

10 Claims, 4 Drawing Sheets

(56) References Cited

U.S. PATENT DOCUMENTS

2003/0189712 A1    10/2003  Pepper et al.
2009/0177098 A1*   7/2009   Yakubo .................... A61B 3/12
                                                        600/504

FOREIGN PATENT DOCUMENTS

WO      WO 01/91661 A1      12/2001
WO      WO 2010/085650 A2    7/2010

OTHER PUBLICATIONS

Written Opinion (PCT/ISA/237) dated Sep. 7, 2012 (Five (5) pages).

* cited by examiner

SPECKLE INTERFEROMETRIC METHOD AND SYSTEM FOR DETECTING A MOVEMENT OF A SURFACE

BACKGROUND AND SUMMARY OF THE INVENTION

The invention concerns a method and an apparatus for detecting a movement of a surface which is irradiated with a coherent light beam emitted especially from a laser wherein variations caused by said movement in a speckle pattern of the reflected light beam are detected.

Such a method and system are known from WO 79/00841 and are used for the measurement of the vibration of an eardrum, wherein the vibration of the eardrum are caused by the application of successively different sound frequencies. The known detector which is placed near the irradiated surface is able to measure exposed structures.

In ophthalmology, it is known (WO 01/91661 A1) to use laser systems in the therapy of retinal diseases, especially of dysfunctional retinal pigmentary epithelium (RPE). During the irradiation, the targeted disease areas of the eye fundus can be thermally sclerosed and, as a result of the subsequent regeneration and lateral proliferation of RPE cells in the sclerotic zones, a substantial restoration of the intact RPE is possible. The selective RPE therapy (SRT) avoids damage to the RPE environment.

In the application of SRT, a burst, i.e. a pulse sequence, of approximately 30 laser pulses with a pulse duration, in each case, of 1.7 µs in the green spectral range and with a pulse sequence rate of 100 Hz at a wavelength of 527 nm is used. Natural and numerous variations to these treatment parameters are also possible. For the thermotherapy of biological tissue, particularly of the eye fundus, clear preference is given to pulse durations of few microseconds. As a result of the strong pigmentation of the RPE approximately 50% of the incident light in the green spectral range is absorbed by the pigment granules (melanosomes) in the RPE cells. High temperatures occur in the RPE in the case of corresponding irradiation (approx. 600 mJ/cm$^2$ per pulse), which lead to intracellular microvaporization on the strongly heated RPE melanosomes.

Resulting micro-bubbles increase the cell volume for microseconds and in all probability ultimately lead to the disruption and disintegration of the RPE cells. The irradiation threshold for cell damage can drop significantly through the application of multiple pulses. There is a considerable variation between patients concerning the prerequisites for laser therapy (e.g. transparency of the lens or glass body, pigmentation of the retina) in connection with eye fundus treatment. Research results show that the necessary pulse energies for producing RPE effects vary intra-individually by up to 100% and inter-individually to an even greater extent. Existing experience shows that the pulse energy must be no more than a factor of two above the threshold pulse energy for producing RPE damage, or otherwise visible damage recurs to the retina.

EP 1 643 924 B1 describes a dosimetry control which detects the thermally induced bubble formation in the irradiated tissue to provide a signal for adjusting the energy of the light beam irradiating the tissue. The detecting device can be either a pressure transducer or a piezo-ceramic pressure sensor or a photo-detector.

The problem to be solved by the invention is to provide a method and a system to detect variations at the surface of an object irradiated by a coherent light beam with a small technical expenditure.

The invention provides a method for detecting a movement of a surface on an irradiated sample, especially on a biological tissue at the fundus of an eye. The method comprises the steps of irradiating said surface with a coherent light beam, detecting variations caused by said movement in a speckle pattern produced by reflections of said light beam at said surface, selecting a single speckle from said speckle pattern, and detecting said variations at the selected speckle.

The invention provides a system for detecting a movement of a surface on an irradiated sample, especially on a biological tissue at the fundus of an eye. The system comprises a light source, especially a laser, emitting a coherent light beam, a light guiding path along which the coherent light beam is directed onto said surface, and a detector, especially a photo-detector adapted to detect variations caused by said movement of the surface at a single speckle selected from a speckle pattern produced by the light beam reflected from the irradiated surface.

The coherence length of the irradiating light beam is greater than the optical path length difference to be measured. For irradiating the surface especially a surface at the fundus of an eye, the irradiating light beam and the light beam reflected at the irradiated surface are guided through a confocal light path. Preferably, the irradiating light beam and the reflected light beam are guided by means of a multi-mode optical fiber, which is intrinsic confocal with the irradiated area so that all points of the irradiated spot are imaged back into the optical fiber without any additional adjustment. The reflected light beam can be split from the irradiating light beam for the detection of especially the variations of the intensity of the reflected light at the selected speckle. The variation of the speckle corresponds to changes at the irradiated area. The measurement of the speckle variations is performed phase-sensitively preferably by means of a photo-detector, especially fast photodiode. It is possible to measure very small changes on the irradiated area, for instance in the magnitude of the wavelength of the irradiating light.

Preferably, the frequency of the detected variation at the selected speckle is correlated to the velocity of a change, especially of the movement at the irradiated surface. This correlation enables to conclude to the origin which caused the variation or the change at the irradiated area, especially if the change or the movement of the surface is caused by the irradiating light beam.

The invention is preferably used to perform a therapy of eye diseases by means of selective retina therapy (SRT). SRT performs a selective microphotocoagulation for degradation of the retinal pigmentary epithelium (RPE), wherein a laser, especially a frequency-doubled Nd:YAG-laser, emitting short pulses, for instance of 1.7 µs or from 1 µs to few µs, in the green space, for instance at a wavelength of 527 nm is used. The fundus of the eye is irradiated with a spot size of about 200 µm. The incident light is absorbed by the melanosomes of the RPE, which leads to an intracellular microvaporization on the heated RPE melanosomes and the creation of micro-bubbles which cause damage to the cells within the irradiated area. This selective cell damage initiates proliferation and migration of RPE-cells from the environment in the damaged area to obtain an irradiation-induced regeneration of the RPE.

The invention enables an accurate dosimetry for the blind treatment of the selective RPE therapy (SRT) by the immediate on-line detection of the bubble formation which can be achieved just after a single pulse within SRT-pulse sequence of for instance about 30 pulses.

During the irradiation, the local heating produces a thermoelastic expansion of the heated tissue. If the formation of micov-bubbles occurs during the irradiation, the velocity of the changes or variations of movement of the irradiated surface are quicker than the thermoelastic expansion of the heated tissue. The changes of the optical path length created by the cavitation bubble and the movement of the surface of the cavitation bubble enables a phase sensitive detection of the bubbles which appear as fast varying signal components. This ability also offers the possibility to detect thermal expansions of cell components, before cavitation bubbles occur. The speckles of the reflected light beam, especially the detected light intensity varies accordingly with an increased frequency within the MHz-region. The frequency of the variation of the light intensity in the speckle pattern, especially of the selected single speckle is correlated with the velocity of the changes at the irradiated area and can provide indication of the bubble-formation.

In order to achieve an adjustment of the energy for the irradiating light beam, one or more test irradiations causing the movement of the illuminated surface can be performed and the energy of the irradiating light beam is determined, when a predetermined variation at the selected speckle occurs.

To achieve an accurate dosimetry for the selective retina therapy (SRT), one or more test irradiations, starting with an energy for the irradiating light beam below the therapeutical window used for SRT can be performed with increasing energy. When the bubble formation is indicated by the predetermined variation, especially the frequency of light intensity variations at the selected speckle, the lower limit of therapeutical energy window within which SRT can be conducted is achieved. The SRT can then be started automatically or by the physician.

In order to compensate the influence of sources disturbing the measurement, the total intensity of the reflected light at all speckles of the speckle pattern can be integrally measured additionally and the modified intensity of light measured at the selected speckle can be normalized with respect to the total intensity.

Additionally to the above explained SRT, the invention can be applied at the photocoagulation of the retina. U.S. Pat. No. 6,830,567 B2 discloses a non-invasive temperature determination during the photocoagulation of the retina, wherein the tissue expansions are measured by means of an optical or a pressure (acoustical) sensor. The present invention provides an alternative measurement of temperature during the retina photocoagulation. The expansion of the tissue is in the region of 100 μm which is within the measurement sensitivity of the inventive detecting system. The thermal expansion of the treated retinal area can be determined by the variation of the light intensity at the selected single speckle and therefrom the average temperature within the irradiation spot can be calculated. The above explained online-dosimetry can be used for the retina coagulation as well.

Generally, the invention can be used for the optical measurement of sample variations having a high time resolution, for instance with respect to path length, distance, expansion, variations of scattering in the sample volume, wherein the measured sample has an at least slightly scattering or reflecting surface or sample volume to form a speckle pattern.

BRIEF DESCRIPTION OF THE DRAWING FIGURES

The invention will become more readily apparent from the following detailed description of currently preferred embodiments thereof when taken in conjunction with the accompanying drawings.

FIG. 1 shows a first embodiment;
FIG. 2 shows a second embodiment;
FIG. 3 shows a third embodiment
FIG. 4 shows a sub-threshold detection signal; and
FIG. 5 shows an above-threshold detection signal.

DETAILED DESCRIPTION

The illustrated systems of the FIGS. 1 to 3 include a light source 1 which is designed as a laser beam source emitting a coherent light beam 9. The light beam is guided along a light path 2 and directed onto a surface 3. The irradiated surface 3 is in the illustrated embodiment the retina of an eye 8.

The light path 2 includes an optical fiber 5 of the multi-mode type into which the emitted light beam 9 is coupled via a focusing lens 17. The end of the optical fiber 5 is coupled by means of a fiber coupler 13 into the irradiation optics of a slit lamp 10 through which the emitted light beam is guided for the irradiation of the surface 3. The irradiation optics of the slit lamp 10 includes the lens system 14 and the mirror 15 to figure the fiber surface preferably in different sizes in the figure-plane of the slit lamp 10. The light guiding path 2 of the illustrated embodiment includes further a contact lens 11 which guides the light beam leaving the slit lamp 10 onto the surface 3 of the retina. The optical fiber 5, a fiber optic coupler 6 and the fiber coupler 13 can be integrated into a fiber optic coupling unit. The slit lamp 10 can be used in such an arrangement for scanning the light beam over the area of the surface 3, which is to be irradiated.

The light beam is reflected and/or scattered at the irradiated surface 3 and is guided back confocally through the irradiation optics of the slit lamp 10 and in the embodiment of FIG. 1, coupled by the fiber coupler 13 into the optical fiber 5. The optical fiber 5 includes a fiber optic coupler 6 from which a portion of the reflected light including a speckle pattern is guided in a detecting arm 19 to a detector 4. The detector 4 is preferably designed as a fast photodiode. By means of an aperture 12 a single speckle can be selected from the speckle pattern of the reflected light beam. Smallest changes in the spot at the irradiated area on the surface 3 cause a great modification of the selected single speckle, especially of its light intensity which is measured by the detector 4.

In the embodiment of the FIG. 2, the reflected and/or scattered light beam is reflected by a beam splitter 18 into a detecting arm 19. The beam splitter 18 is placed within the irradiation optics which is used to link the laser beam into the slit lamp 10 to create a light spot of the irradiating light in the figure-plane of the slit lamp 10. The detecting arm 19 includes an aperture 20 to adjust the intensity of the reflected light. A focusing lens 21 collimates the light coming from the aperture 10. A pin hole 22 is placed in the focal plane of the focusing lens 21. By varying the aperture the number of speckles can be adjusted, especially to a single speckle.

In the embodiment of the FIG. 3, the emitted light beam 9 is applied into the fiber 5 via a beam splitter 23 and a focusing lens 17 and is guided in the same way as in the embodiments of the FIGS. 1 and 2 onto the surface 3 of the retina. The reflected and/or scattered light beam is split by the beam splitter 23 into the detecting arm 19 which is confocal to the exit of the fiber 5. The detecting arm includes like the embodiment of FIG. 2, the focusing lens 21, the pinhole 22 in the focal plane of the lens 21 and the detector 4.

The before explained embodiments of the FIGS. 1 to 3 include one detector 4 which detects the variation at a single selected speckle. It is also possible to use more than one detector 4, wherein each detector detects the variations at preferably one single selected speckle. For each detector a respective speckle can be chosen from the speckle pattern.

A further improvement of the phase sensitivity can be achieved by using additionally a second detector, especially a photo-diode which measures integrally over all speckles of the speckle pattern and by using the difference signal of the two detectors to obtain exclusively the modulated portion of the selected single speckle. This operation can be done by an operational amplifier with high common-mode rejection (CMR) implemented in an analyzing means 7 connected to the detectors. Furthermore, it is possible to use a balanced detector in which the two photo-diodes have directly connected anode and cathode. If the reflected light includes a high non-modulated amount of light, for instance if the treated eye has a cataract, the use of the additional second photo-diode for the explained normalization of the detected signal is preferred.

The measuring system having the confocal light path can be designed also without the use of fiber optics, wherein the reflected light having the speckle pattern is imaged in an image plane and the modulated single speckle is used for the detection.

Figure 4:
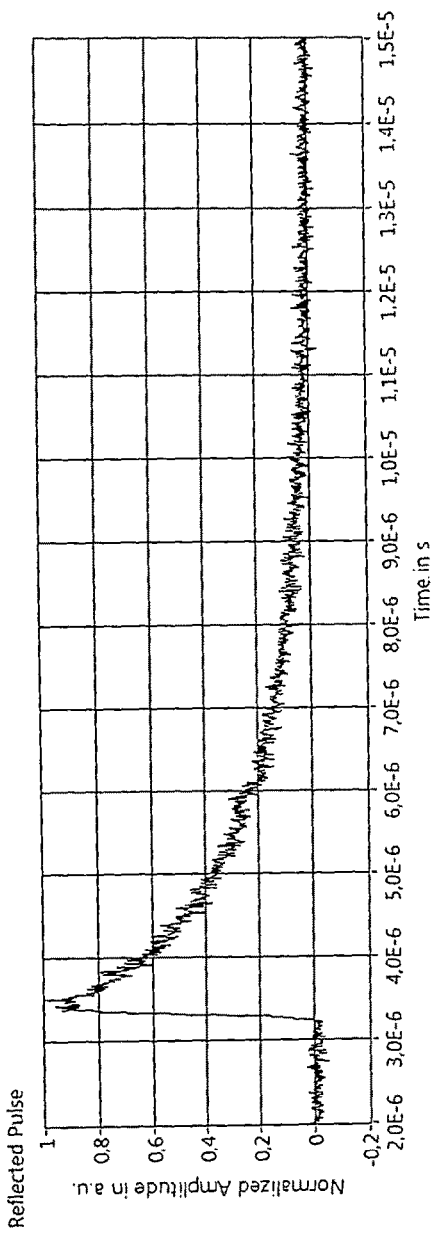
FIG. 4 illustrates the detection of the reflected pulses during the irradiation of RPE in a region below the threshold energy (sub threshold) which creates cavitation bubbles.
Figure 5:
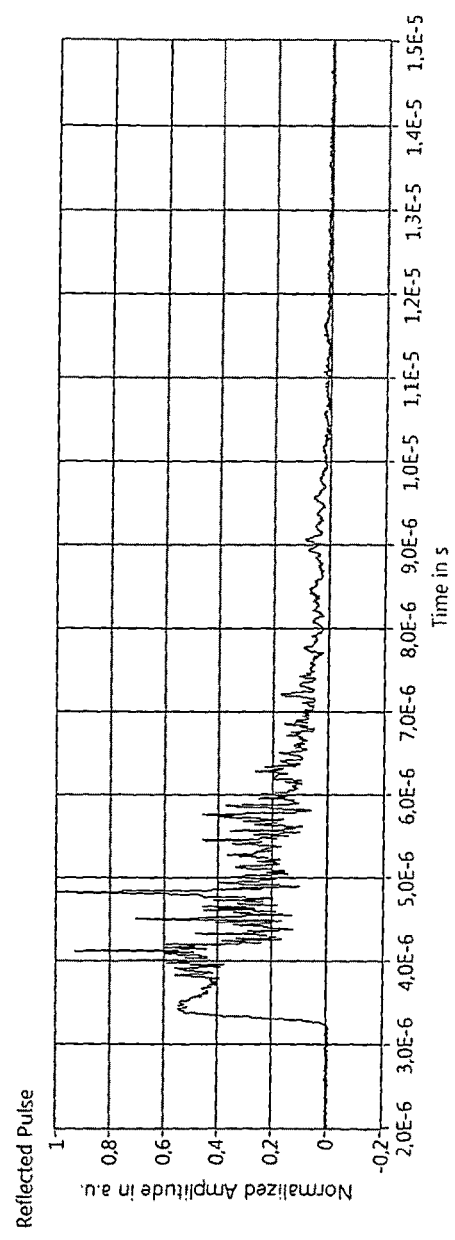
FIG. 5 illustrates the detection of the reflected pulses during the irradiation of RPE above the threshold energy (above threshold) which creates cavitation bubbles. The modulations of the detected signal indicate bubble formation.

The time units "E-6" mean $10^{-6}$ in the FIGS. 4 and 5.

Figure 1:
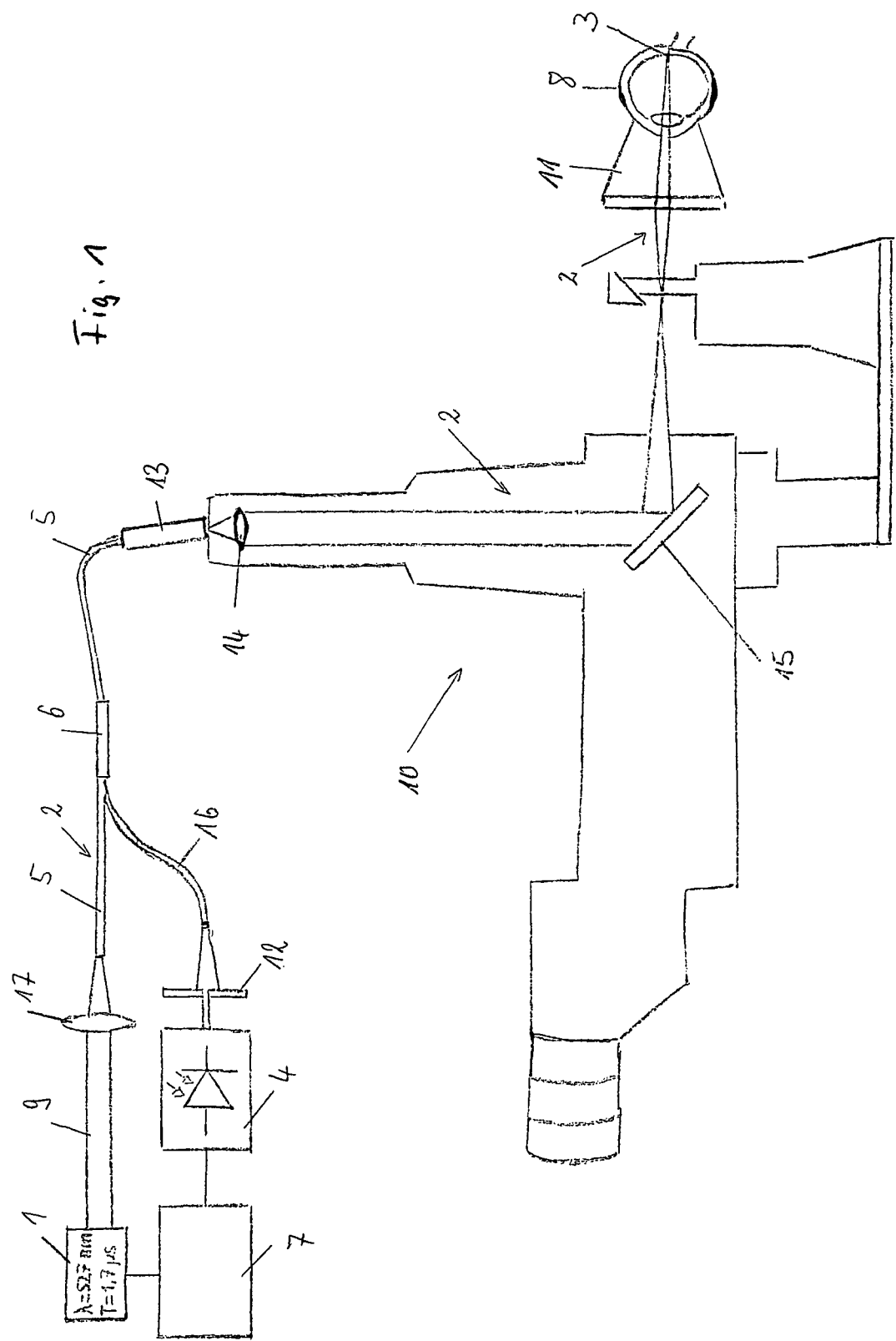
Figure 2:
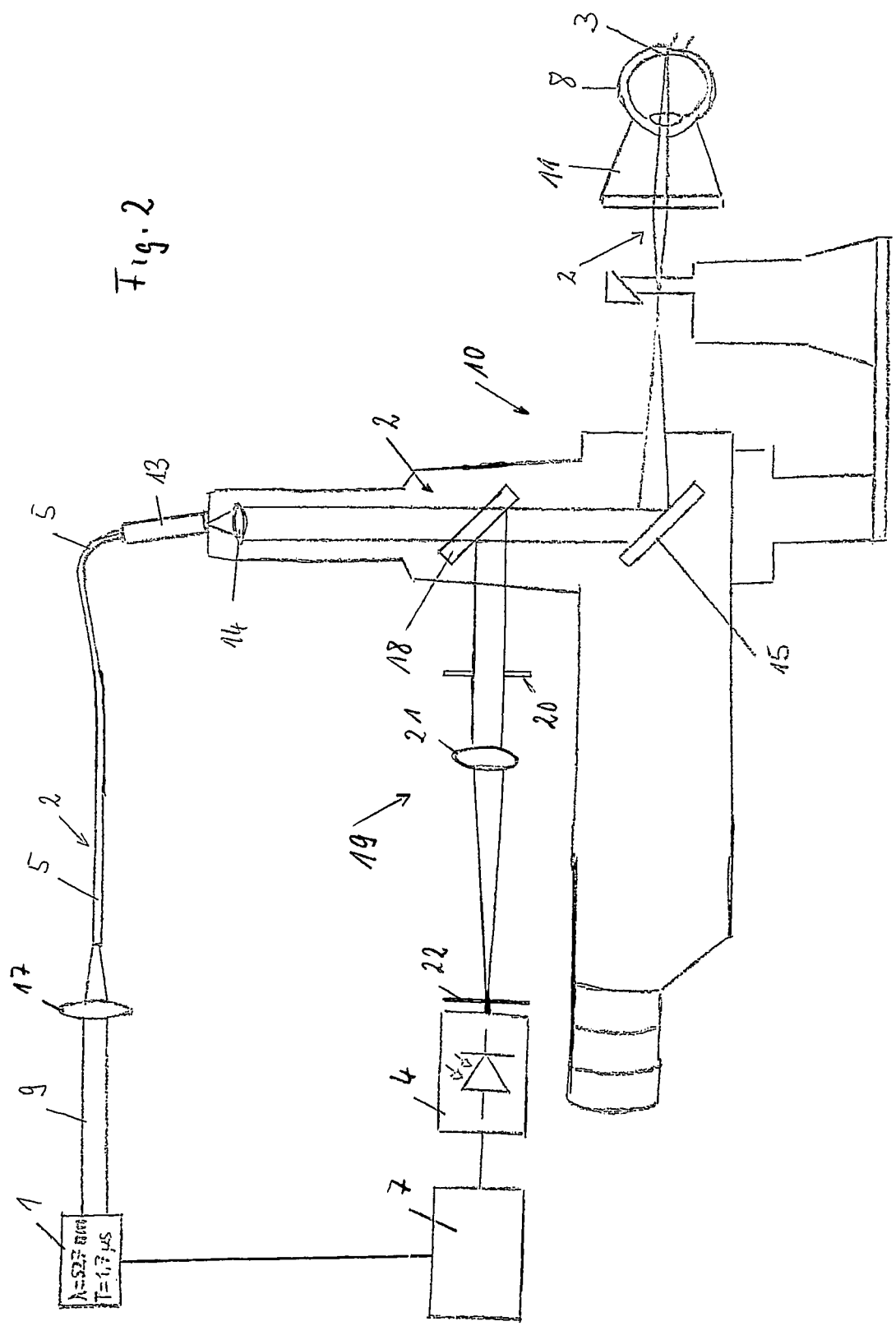
Figure 3:
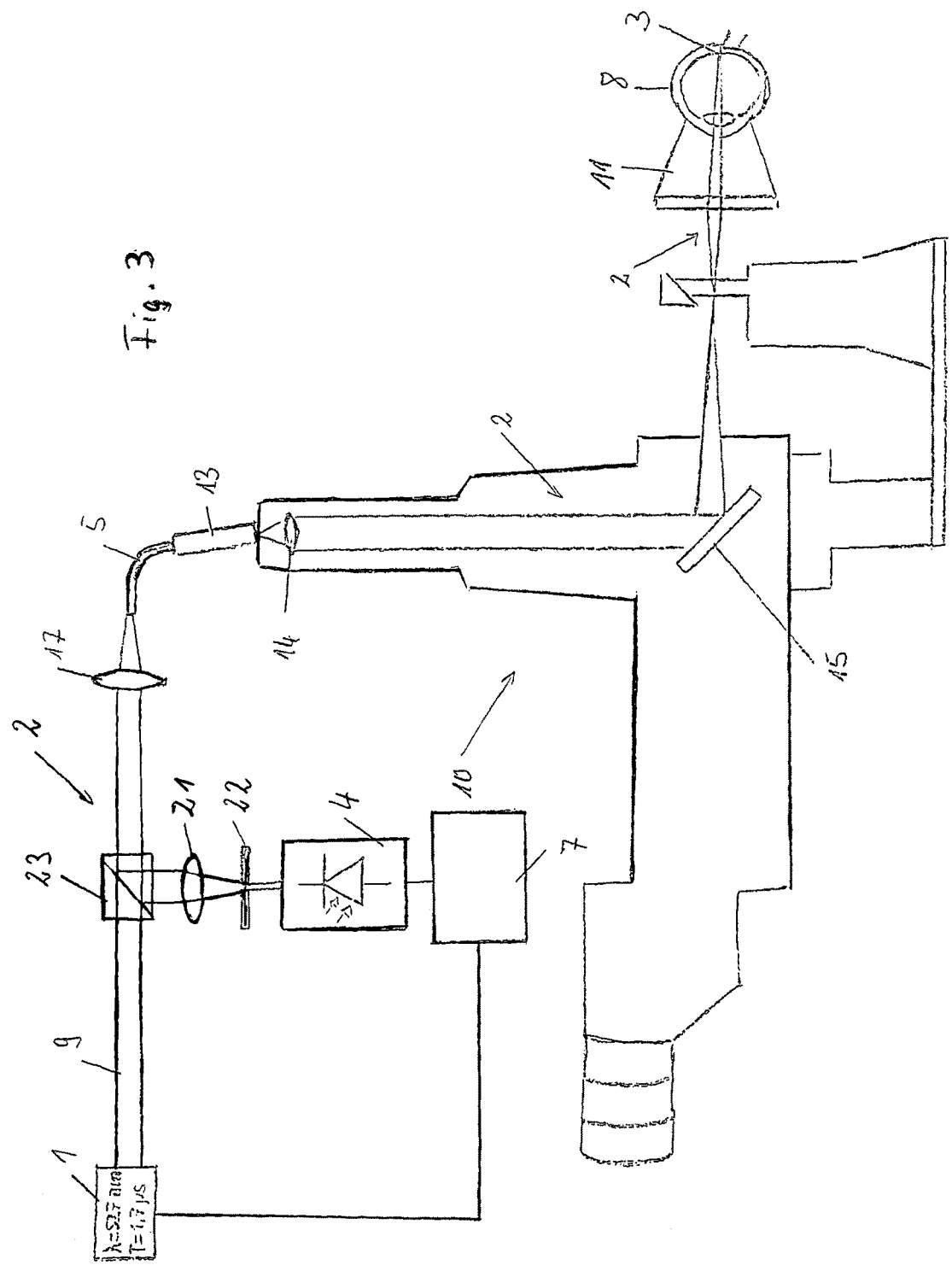

The illustrated embodiments of FIGS. 1 to 3 can be used for the selective retina therapy (SRT) and for the photocoagulation of the retina. The used light source is preferably a frequency-doubled Nd:YAG-laser emitting pulses of about 1.7 µs or of a few µs in the green region, for instance with a wave length of 527 mm. The spot diameter at the irradiated area is about 200 µm. Each treatment sweeps can include for instance 30 pulses.

From the modulation of the detected single speckle the expansion of the irradiated tissue area of the retina can be calculated by the analyzing means 7, which are connected to the detector 4, and a control of the energy of the emitted light beam 9 can be achieved during the photocoagulation of the retina. Additionally, the temperature in the irradiated area can be derived from the deletion of the modulated speckle as well.

For the selective retina therapy, the bubble-formation is calculate in the analyzing means 7 from the modulation of the detected single speckle and the energy of the emitted light beam 9 can be controlled in an appropriate manner. The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE NUMBERS 1 light source (laser)
2 light guiding path
3 irradiated surface
4 detector
5 optical fiber
6 fiber optic coupler
7 analyzing means
8 eye
9 emitted light beam
10 slit lamp
11 contact lens
12 aperture
13 fiber coupler
14 lens
15 mirror
16 detecting arm
17 focusing lens
18 beam splitter
19 detecting arm
20 aperture
21 focusing lens
22 pin hole
23 beamsplitter

The invention claimed is:

1. A system for treatment of an eye, comprising:
 a laser light source configured to emit a coherent laser light beam;
 a light guiding path configured to direct the coherent laser light beam onto a surface of a biological tissue of the eye, wherein the coherent laser light beam is capable of causing a movement of the surface of the biological tissue, wherein the biological tissue is heated by the coherent laser light beam and the movement of the surface of the biological tissue is caused by an expansion of the biological tissue caused by heating the biological tissue; and
 a detector configured to detect variations caused by said movement of the surface of the biological tissue at a single speckle selected from a speckle pattern produced by the coherent laser light beam reflected from the surface of the biological tissue.

2. The system of claim 1, wherein the detector is one of a plurality of detectors, each of which is configured to detect the variations at a single selected speckle.

3. The system of claim 1, further comprising an aperture, which is arranged before the detector.

4. The system of claim 1, further comprising:
 analyzing means connected to the detector, wherein the analyzing means are configured to correlate a frequency of a light intensity variation measured at said single speckle with a velocity of the movement of the surface of the biological tissue onto which the coherent laser light beam is directed.

5. The system of claim 4, wherein the analyzing means are additionally configured to compare the frequency of the light intensity variation measured at the single speckle or a correlated velocity of the movement of the surface of the biological tissue with a predetermined frequency or velocity and wherein the analyzing means are configured to adjust energy of the laser light source, when said predetermined frequency or velocity is obtained while directing the coherent laser light beam onto the surface of the biological tissue.

6. The system of claim 1, wherein the coherent laser light beam is configured to perform a therapeutic treatment of the biological tissue.

7. The system of claim 1, wherein the coherent laser light beam is configured to perform a therapeutic treatment on the retina of the eye.

8. The system of claim 1, wherein the coherent laser light beam is configured to perform a selective retina therapy on the eye.

9. The system of claim 1, wherein the coherent laser light beam is configured to perform a photocoagulation on the retina of the eye.

10. The system of claim 1, wherein the system is combined with a slit lamp device, and wherein a light spot of the coherent laser light beam is created in the figure plane of the slit lamp device.

\* \* \* \* \*